United States Patent
Froggett et al.

(10) Patent No.: US 6,949,650 B2
(45) Date of Patent: Sep. 27, 2005

(54) PROCESS FOR THE RACEMIZATION OF 1-BENZYL-4-(4-FLUOROPHENYL)-3-HYDROXYMETHYL-1,2-3,6-TETRAHYDROPYRIDINE TO BE USED AS INTERMEDIATE IN THE SYNTHESIS OF PAROXETINE

(75) Inventors: Jayne Froggett, Oakerthorpe Alfreton (GB); Dean Riley, Nottingham (GB); Andrew Turner, Holmes Chapel (GB)

(73) Assignee: Aesica Pharmaceuticals Ltd., Cramlington (GB)

( * ) Notice: Subject to any disclaimer, the term of this patent is extended or adjusted under 35 U.S.C. 154(b) by 135 days.

(21) Appl. No.: 10/362,531

(22) PCT Filed: Aug. 30, 2001

(86) PCT No.: PCT/EP01/09998

§ 371 (c)(1),
(2), (4) Date: Feb. 25, 2003

(87) PCT Pub. No.: WO02/18338

PCT Pub. Date: Mar. 7, 2002

(65) Prior Publication Data

US 2004/0014786 A1 Jan. 22, 2004

(30) Foreign Application Priority Data

Aug. 30, 2000 (GB) .......................................... 00211474

(51) Int. Cl.$^7$ ............................................. C07D 221/02
(52) U.S. Cl. ...................................... 546/112; 546/240
(58) Field of Search ................................. 546/112, 240

(56) References Cited

U.S. PATENT DOCUMENTS 2,748,140 A * 5/1956 Schmidle et al. ............ 546/342
4,007,196 A     2/1977 Christensen et al. ........ 546/197

FOREIGN PATENT DOCUMENTS

| WO | 96/36636 | 11/1996 |
| WO | 97/24323 | 7/1997 |
| WO | 98/01424 | 1/1998 |
| WO | 98/52920 | 11/1998 |

OTHER PUBLICATIONS

Exhibit A and B, search results.*
Mesnard et al. "Action of p–toluensulfonyl chloride . . . " CA 60:26971 (1964).*
Sjoegreen et al. "A process of making . . . " CA 124:260382 (1996).*
Choudary et al. "Montmorillonite clay catalyzed . . . " CA 133:362452 (2000).*
ActaChem.Scand,vol. 50,No. 2(1996) 164–169,Engelstoft et al.
J.LabelledCompounds . . . , vol. 33,No. 8,1993, 783–794 Willocks et al.

* cited by examiner

Primary Examiner—Celia Chang
(74) Attorney, Agent, or Firm—Novak Druce & Quigg

(57) ABSTRACT

A process for the racemization of enantiomerically enriched 1-benzyl-4-(4-fluorophenyl)-3-hydroxymethyl-1,2,3,6-tetrahydropyridine which is a useful intermediate in the preparation of paroxetine. Formula (A) means that the compound (I) has an enantiomeric excess of one enantiomer over the other enantiomer. $R_1$ and $R_2$ are defined as in claim 1.

7 Claims, No Drawings

PROCESS FOR THE RACEMIZATION OF 1-BENZYL-4-(4-FLUOROPHENYL)-3-HYDROXYMETHYL-1,2-3,6-TETRAHYDROPYRIDINE TO BE USED AS INTERMEDIATE IN THE SYNTHESIS OF PAROXETINE

This application is a 371 of PCT/EP01/09998, filed Aug. 30, 2001, and claims priority to GB0021147.4, filed Aug. 30, 2000.

This invention relates to a process for the racemisation of enatiomerically enriched 1-benzyl-4-(4-fluorophenyl)-3-hydroxy-methyl-1,2,3,6-tetrahydropyridine which is a useful intermediate in the preparation of paroxetine.

U.S. Pat. No. 4,007,196 discloses compounds which possess anti-depressant activity. One particular compound disclosed in this patent is known as paroxetine and has the structure A below:

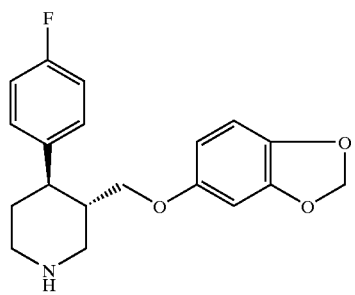

A

This compound has been found to be especially useful in the treatment of depression and several processes have been described to prepare this important compound. WO 96/36636 (which is incorporated herein by reference) discloses one such process. WO 98/52920 (which is incorporated herein by reference) discloses a process for preparing a useful intermediate in the preparation of paroxetine.

WO 98/01424 (which is incorporated herein by reference) discloses a process for the preparation of racemic trans-1-benzyl-3-hydroxymethyl-4-(4-fluorophenyl) piperidine in which 4-(4-fluoro-phenyl)-N-benzyl-1,2,5,6-tetrahydropyridine is reacted with formaldehyde in acidic medium via the Prins reaction to give the desired product. One of the optional next stages for the process is the resolution of this compound with an optically active acid, preferably dibenzoyltartaric acid ordi-p-toluyl-tartaric acid, to give the individual enantiomers of trans-1-benzyl-3-hydroxymethyl-4-(4-fluorophenyl)piperidine. Clearly this process is wasteful in that 50% of the material is then discarded as only one enantiomer, the (+)-enantiomer, is further processed to give paroxetine. It would be desirable to be able to racemise the unwanted enantiomer and to then resolve the racemic mixture to produce more of the desired enantiomer. However, many attempts by the present applicants to find a satisfactory racemisation process ended in failure.

Surprisingly an efficient process for carrying out this racemisation has now been found.

The present invention provides a process for the racemisation of a compound of formula I comprising the steps of
a) reacting an enantiomerically enriched compound of formula I

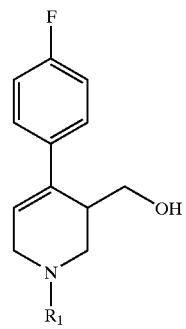

I in which $R_1$ represents an amine protecting group, with a compound of formula II $$R_2X \quad \text{II}$$

in which $R_2$ represents a group of formula $R_3SO_5$—in which $R_3$ represents optionally substituted phenyl, a $C_{1-6}$alkyl group or a trifluoromethyl group and X represents halo to give a compound of formula III

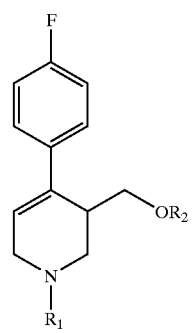

III in which i) $R_2$ represents a group of formula $R_3SO_2$—in which $R_3$ represents optionally substituted phenyl, a $C_{1-6}$alkyl group or a trifluoromethyl group,
b) reacting the compound of formula III with a compound of formula IV

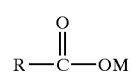

IV in which M represents an alkali metal and R represents H, a $C_{1-6}$alkyl group, optionally substituted phenyl or an (optionally substituted phenyl)hydroxy$C_{1-6}$alkyl group to give a substantially racemic compound of formula V

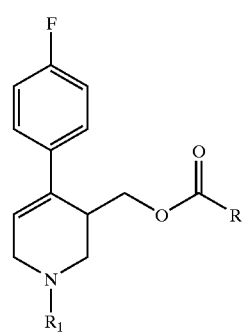

V in which $R_1$ and R are as previously defined; and c) reacting the compound of formula V with a hydrolysing agent to give a substantially racemic compound of formula I.

It will be appreciated by those skilled in the art that the compounds of formula III may also be prepared by reacting a compound of formula I with an halogenating agent to give a compound of formula Ia

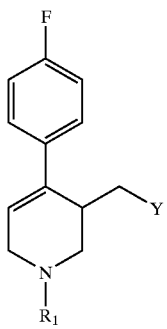

Ia in which Y is halo. The compound of formula Ia may then be reacted with a salt of formula $MOR_2$ in which $R_2$ is as previously defined to give a compound of formula III. This alternative process also forms part of the present invention.

Suitably halogenating agents include hydrogen bromide, hydrogen chloride, oxalyl chloride, phosphorus pentachloride, phosphorus trichloride, phosphorus pentabromide, phosphorus tribromide, bromine, phosphorus oxychloride, phosphorus oxybromide, thionyl chloride, thionyl bromide, a mixture of carbon tetrachloride and triphenylphosphine, a mixture of tetrabromomethane and triphenyl-phosphine, N-bromosuccinimide and N-chlorosuccinimide. Preferably the halogenating agent is thionyl chloride or thionyl bromide.

Whilst not bound by theory, it is believed that the mechanism of the above racemisation process involves an intermediate salt which is a compound of formula IIIa

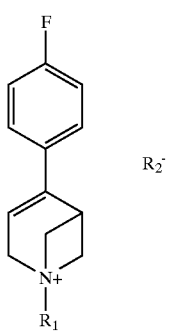

IIIa in which $R_1$ is as previously and $R_2^-$ is an anion of formula $R_3SO_2^-$. The compound of formula IIIa in which $R_2^-$ represents the anion $^-OSO_2CF_3$ and $R_1$ represents benzyl has been isolated from the reaction mixture and identified. In addition the product of formula IIIa where $R_2^-$ represents $^-OSO_2$-Ph has been identified in the reaction solution by nuclear magnetic resonance spectroscopy.

In a preferred aspect the present invention provides a process for the racemisation of a compound of formula I comprising the steps of a) reacting an enantiomerically enriched compound of formula I

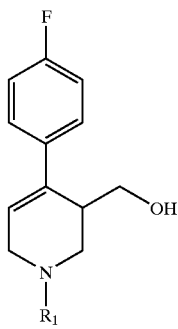

I in which $R_1$ represents an amine protecting group, with a compound of formula II $R_2X$  II in which $R_2$ represents a group of formula $R_3SO_2$—in which $R_3$ represents optionally substituted phenyl, a $C_{1-6}$alkyl group or a trifluoromethyl group and X represents halo to give a compound of formula III

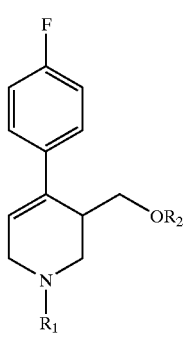

III in which i) $R_2$ represents a group of formula $R_3SO_2$—in which $R_3$ represents optionally substituted phenyl, a $C_{1-6}$alkyl group or a trifluoromethyl group, wherein the compound of formula III is in equilibrium with a compound of formula IIIa

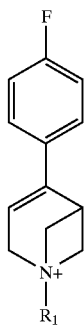

IIIa in which $R_1$ represents an amine protecting group and $R_2^-$ is an anion of $R_2$ b) reacting the compound of formula IIIa with a compound of formula IV

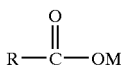

in which M represents an alkali metal and R represents H, a $C_{1-6}$alkyl group, optionally substituted phenyl or an (optionally substituted phenyl)hydroxy$C_{1-6}$alkyl group to give a substantially racemic compound of formula V

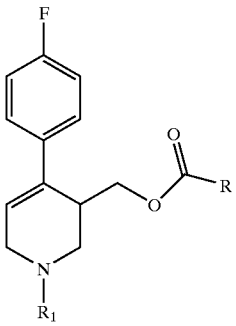

in which $R_1$ and R are as previously defined; and
c) reacting the compound of formula V with a hydrolysing agent to give a substantially racemic compound of formula I.

In a further aspect the present invention provides compounds of formula IIIa

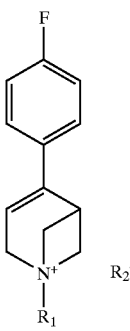

in which $R_1$ represents an amine protecting group and $R_2$ is a previously stated. Preferably $R_1$ represents benzyl or a $C_{1-6}$-alkyl group. More preferably $R_1$ represents benzyl, methyl or ethyl. Most preferably $R_1$ represents benzyl. Preferably $R_2^-$ is a benzene-sulphonate anion, a methanesulphonate anion or a trifluoro-methanesulphonate anion.

Preferably the amino protecting group is one which is inert to reduction by a metal hydride. More preferably the amine protecting group is selected from a) allyl, b) benzhydryl, c) methoxymethyl, d) benzyloxymethyl, e) tetrahydropyranyl, f) an optionally substituted benzyl group, g) di(p-methoxy-phenyl)methyl, h) triphenylmethyl, i) (p-methoxyphenyl)diphenyl-methyl, j) diphenyl-4-pyridylmethyl, k) a $C_{1-6}$alkyl group, for example methyl or ethyl, l) a trifluoro $C_{1-4}$alkyl group, m) an alkynyl group or n) p-methoxybenzyl. Most preferably the amine protecting group is a benzyl group which is optionally substituted on the phenyl ring by one or more of the following groups: a $C_{1-4}$alkyl group, a $C_{1-4}$alkoxy group, halo or nitro. Especially preferably $R_1$ represents benzyl.

The term optionally substituted phenyl means phenyl substituted by one or more of the following: a) a $C_{1-6}$alkyl group, b) nitro or c) halo.

The term enantiomerically enriched should be understood to mean that the compound of formula I has an enantiomeric excess of one enantiomer over the other enantiomer in the range of 1 to 100%, preferably an enantiomeric excess in the range of 50 to 100%, and more preferably an enantiomeric excess in the range of 70 to 100%.

Suitably either enantiomer may predominate in the enantiomerically enriched compound. Preferably the predominant enantiomer is the (+) enantiomer. More preferably the predominant enantiomer is the (−)enantiomer.

The term substantially racemic means that there is an enantiomeric excess of less than 20% preferably less than 10% and most preferably less than 5%.

Preferably $R_3$ represents methyl or phenyl optionally substituted by a methyl group, a nitro group or halo. More preferably $R_3$ represents methyl, 4-tolyl, 4-nitrophenyl, or 4-bromophenyl.

Suitably the hydrolysing agent includes a basic or acidic hydrolysing agent. Preferred basic hydrolysing agents include aqueous sodium hydroxide, aqueous ammonia, aqueous potassium carbonate, aqueous potassium bicarbonate, aqueous sodium bicarbonate, aqueous sodium carbonate, potassium hydroxide, aqueous potassium hydroxide and aqueous lithium hydroxide. Preferred acidic hydrolysing agents include hydrochlorid acid, hydrobromic acid and sulphuric acid. Most preferably the hydrolysing agent is aqueous hydrochloric acid or aqueous sodium hydroxide solution.

In another aspect the present invention provides novel compounds of formula III and V in which $R_1$ and R are as previously defined which are useful as intermediates in the preparation of paroxetine. Preferably $R_1$ is benzyl. Preferably R is methyl. Preferably M is potassium.

In yet another aspect the present invention provides a process for the preparation of paroxetine from a compound of formula I according to the methods described in WO 96/36636, and WO 98/01424 characterised in that the compound of formula I was prepared by racemisation of an enantiomerically enriched compound of formula I by the process of the present invention. The paroxetine may be obtained as the hydrochloride salt as the anhydrous form or the hemihydrate or other solvate. The process of the present invention may also be used in conjunction with the process described in WO 98/52920 to prepare an intermediate which may be further processed as described below to produce paroxetine. These combination processes also form part of the present invention.

The process of the present invention is advantageous because it provides a pure precursor to paroxetine. Paroxetine may be obtained in a pure form from compounds of formula I by a) conversion of the hydroxy group into a leaving group, for example halo or tosyloxy, b) reaction with sesamol or a salt thereof, c) removal of the protecting group $R_1$ by conventional means for example by hydrogenolysis when $R_1$ is benzyl and optionally d) salt formation, for example the hydrochloride salt as the anhydrous form or the hemihydrate.

The invention is illustrated by the following Examples which are given by way of example only. The final product of each of these Examples was characterised by one or more of the following procedures: gas-liquid chromatography: high performance liquid chromatography: elemental analysis; nuclear magnetic resonance spectroscopy and infrared spectroscopy.

EXAMPLES

Example 1

Triethylamine (3.2 ml) was added to a solution of (+)-benzyl-3-hydroxymethyl-4-4-(4-fluorophenyl)-1,2,3,6-tetrahydropyridine (21.7 g) in dichlormethan (87 ml) at ambient temperature and then benzenesulphonyl chloride (11.3 ml) was added to the solution with stirring. The mixyture was stirred at ambient temperature for 18 hours. Water (b74 ml) was added and the mixture was stirred for 10 minutes. The organic layer was separated off, washed with water (74 ml), then dried, filtered and evaporated to give (+)-1-benzyl-4-(4-fluorophenyl) -1,2,3,6-tetrahydropyridine-3-methyl benzenesulphonate.

Example 2

Potassium acetate (1.23 g) was added to a stirred solution of (+)-1-benzyl-4-(4-fluorophenyl)-1,2,3,6-tetrahydropyridine-3-methyl benzenesulphonate (5.0 g) in acetonitrile (50 ml). 18-Crown-6 (0.3 g) was added to the mixture and the mixture was stirred at ambient temperature for 18 hours and then stirred and boiled under reflux 6 hours. The mixture was allowed to cool to ambient temperature and then allowed to stand at this temperature for 64 hours. Water (50 ml) was added, followed by ethyl acetate (50 ml). The mixture was stirred for around 5 minutes. TYhe organic layer was separated, washed with water (50 ml), dried, filtered and evaporated to give (+,−)-1-benzyl-4-(4-fluorophenyl)-1, 2, 3, 6-tetrehydropyridine-3-methyl acetate.

Example 3

Aqueous sodium hydroxide solution (1.84 ml of a 4M solution) was added to a solution of (+,−)-1-benzyl-4-(4-fluorophenyl)-1, 2, 3, 6-tetrahydropyridine-3-methyl acetate (0.5 g) in industrial methylated spirits (5 ml). The mixture was boiled under reflux for 4.25 hours. The mixture was evaporated under reduced pressure and then water (10 ml) and toulene (10 ml) were added to the residue. The organic layer was separated, washed with water (10 ml) then dried, filtered and evaporated to give (+,−)-1-benzyl-3-hydroxymethyl -4-(4-fluorophenyl)-1, 2, 3, 6-tetrahydropyridine (ee 11.6%).

Example 4

Triethylamine (3.2 ml) was added to a solution of (+)-1-benzyl-3-hydroxymethyl-4-(4-fluorophenyl)-1, 2, 3, 6-tetrahydropyridine (5.65 g) in toluene (44.35 g) and the mixture was stirred at ambient temperature. The solution was cooled to 5°C. in an ice/water bath and the methanesulphonyl chloride (1.6 ml) was added dropwise over a minute. The temperature rose to 11°C. over 5 minutes and then dropped to 5°C. over 5 minutes. The mixture was stirred at 0–5°C. for 75 minutes. The mixture was allowed to warm to 10°C. and water (10 ml) was added. The mixture was stirred for 5 minutes and then the organic layer was separated, washed with water (20 ml), and then dried, filtered and evaporated to give (+)-1-benzyl-4-(4-fluorophenyl) -1, 2, 3, 6-tretrahydropyridine-3-methyl methanesulphonate as an oil which solidified on standing. $[\alpha]_D 21.5°C.=+78.2 \pm 1.4$]concentration 2.0735 g per 100 ml of chloroform.

Example 5

Potassium acetate (1.23 g) and 18-crown-6 (0.3 g) were added to a stirred solution of (+)-1-benzyl-4-(4-fluorophenyl)-1,2,3,6-tetrahydropyridine-3-methyl methanesulphonate (4.27 g) in acetonitrile (50 ml) with stirring, The mixture was stirred at ambient temperature for 1.5 hours and then boiled under reflux with scirring for 5 hours, The mixture was allowed to stand at ambient temperature for 64 hours and then boiling under reflux was continued for a further 5 hours. The mixture was cooled to ambient temperature and then ethyl acetate (50 ml) and water (50 ml) were added. The mixture was stirred for approximately 5 minutes and then brine (20 ml) was added to the mixture followed by dry ethyl acetate (10 ml). The organic layer was separated, washed with brine (50 ml), dried, filtered and evaporated to give (+,−)-1-benzyl-4-(4-fluorophenyl-1,2,3,6-tetrahydropyridine-3-methyl acetate.

Example 6

Aqueous sodium hydroxide solution (9.6 ml of a 4M solution) was added to a solution of (+,−)-1-benzyl-4-(4-fluorophenyl)-1,2,3,6-tetrahydropyridine-3-methyl acetate (2.6 g) in industrial methylated spirits (26 ml) with stirring. The mixture was boiled under reflux for 1.5 hours. The mixture was evaporated under reduced pressure and then toluene (40 ml) and water (20 ml) were added. The organic layer was removed, washed with water, and then dried, filtered and evaporated to give (+,−)-1-benzyl-3-hydroxymethyl-4-(4-fluorophenyl)-1,2,3,6-tetrahydropyridine (ee 16.3%).

Example 7

A solution of (−)-enriched)-1-benzyl-3-hydroxymethyl-4-(4-fluoro-phenyl)-1,2,3,6-tetrahydropyridine (19.8 g) in toluene (100 g) which had been previously dried by azeotropic distillation, was stirred at ambient temperature whilst triehylamine (13.9 ml) and benzenesulphonyl chloride (9.9 ml) were added. The mixture was stirred at ambient temperature for 64 hours. Water (64 ml) was added and the mixture was stirred for approximately 15 minutes. The organic layer was separated off, washed with water and a sample (10 ml) was removed for analysis. The remaining toluene solution was boiled under reflux with azeotropic removal of the water using a Dean & Stark apparatus for approximately 15 minutes. The mixture was cooled to ambient temperature and potassium acetate (7.18 g) and propan-2-ol (97.2 ml) were added. The mixture was boiled under reflux for 19 hours, then cooled to 45° C. and ah aqueous solution of sodium hydroxide (66.6 ml of a 4M solution) and water (33 ml) were added. The resulting 2-phase mixture was boiled and stirred under reflux for 1.75 hours. Solvent (60 ml) was removed by distillation and the mixture was allowed to cool to ambient temperature. The organic layer was separated, washed with water then evaporated under reduced pressure to give (+,−)-1-benzyl-3-hydroxymethyl-4-(4-fluoro-phenyl)-1,2,3,6-tetrahydropyridine as an oil (ee 5.4%)

Example 8

Triethylamine (1.39 ml) and benzenesulphonyl chloride (9.9 ml) were added to a solution of (−)-1-benzyl-3-hydroxymethyl-4-(4-fluorophenyl)-1,2,3,6-tetrahydropyridine (19.8 g) made up to 100 g with toluene, with stirring under nitrogen. The mixture was stirred at ambient temperature for 72 hours. Water (64 ml) was added and the mixture was stirred for 15 minutes. The organic layer was separated, washed with water and a small sample of the solution (5 ml) was removed. The remaining toluene solution was stirred while potassium acetate (7.18 g) and 4-methyl-2-pentanol (71 ml) were added. The mixture was then boiled and stirred under reflux with removal of water via a Dean & Stark apparatus for 5.5 hours. The mixture was allowed to cool to ambient temperature and stood at this temperature for 18 hours. Water (64 ml) was added and the mixture was stirred for 5 minutes. The aqueous layer was separated off. The organic layer was returned to the reaction flask and stirred while water (51.2 ml) followed by concentrated hydrochloric acid (28.6 ml) were added. This mixture was boiled under reflux for 1.5 hours. The reaction mixture was cooled to around 40° C. and the concentrated aqueous ammonia (22.1 ml) was added dropwise keeping the temperature below 45° C. More concentrated aqueous ammonia solution (6 ml) was added to give a final pH of 8–9. The reaction mixture was stirred for around 15 minutes and then cooled to ambient temperature. The organic layer was separated, washed with water, dried and evaporated to give (+,−)-1-benzyl-3-hydroxymethyl-4-(4-fluoro-phenyl)-1,2,3,6-tetrahydropyridine (ee 4.4%)

Example 9

Triethylamine (12.9 ml) was added to a solution of (−)-1-benzyl-3-hydroxymethyl-4-(4-fluorophenyl)-1,2,3,6-tetrahydropyridine (25.0 g) made up to 137 g with toluene, with stirring under nitrogen. The solution was cooled to 5° C. in an ice/water bath and methanesulphonyl chloride (6.6 ml) was added dropwise over 20 minutes keeping the temperature below 10° C. The mixture was stirred at 0–10° C. for 45 minutes. 4-Methyl-2-pentanol (6.5 ml) was added and the mixture stirred for a further 15 minutes. The mixture was allowed to warm to 20° C. and water (40 ml) was added. The mixture was stirred for 15 minutes and then the organic layer was separated, and washed with water (40 ml). The remaining toluene solution was stirred while potassium acetate (9.5 g) and 4-methyl-2-pentanol (19.5 ml) were added. The mixture was then boiled and stirred under reflux with removal of water via a Dean & Stark apparatus for 15 to 20 hours. The mixture was allowed to cool to 50° C. Water (40 ml) was added and the mixture was stirred for 15 minutes. The aqueous layer was separated off. The organic layer was returned to the reaction flask and stirred while water (12.8 ml) followed by concentrated hydrochloric acid (10.2 ml) were added. This mixture was boiled under reflux for 3 hours. The reaction mixture was cooled to around 40° C. and then concentrated aqueous ammonia (23 ml) was added dropwise keeping the temperature below 45° C. to give a final pH of 8–9. The reaction mixture was stirred for around 15 minutes and then cooled to ambient temperature. The organic layer was separated, washed with water (2×40 ml) and evaporated to give (+,−)-1-benzyl-3-hydroxymethyl-4-(4-fluorophenyl)-1,2,3,6-tetrahydropyridine (ee 9.0%).

Example 10

Triethylamine (1.5 ml) was added to a solution of (+)-1-benzyl-3-hydroxymethyl-4-(4-fluorophenyl)-1,2,3,6-tetrahydropyridine (2.82 g) in toluene (22.18 g) and the mixture was stirred at ambient temperature. The solution was cooled to 5° C. in an ice/water bath and the trifluoromethanesulphonic anhydride (1.8 ml) was added dropwise over 5 minutes. The mixture was stirred at 0° C. to room temperature for 4 hours, then stood for 48 hours. Water (25 ml) was added. The mixture was stirred for 2 minutes and then ethyl acetate and 4M-NaOH were added to dissolve an insoluble oil. The organic layer was separated, washed with water (25 ml), and then dried, filtered and evaporated to give 1-benzyl-4-(4-fluorophenyl)-1-azoniabicyclo[3.1.1]hept-3-ene trifluoro-methanesulphonate as an oil The oil was triturated with 60–80° C. petrol to give a solid.

Example 11

Potassium acetate (0.14 g) was added to a stirred solution of 1-benzyl-4-(4-fluorophenyl)-1-azoniabicyclo[3.1.1]hept-3-ene trifluoromethanesulphonate (0.5 g) in toluene (2.5 ml)

and propan-2-ol (2.5 ml). The mixture was then boiled and stirred under reflux for 24 hours. The mixture was cooled to room temperature and toluene (10 ml) and water (5 ml) were added. The organic layer was separated, dried and evaporated to leave an oil. A solution of the oil in propan-2-ol (2 ml) and toluene (2 ml) was treated with 4M-NaOH (0.4 ml). The mixture was boiled under reflux for 2 hours then cooled to room temperature. Water (5 ml) and toluene 95 ml) were added. The organic layer was separated, washed with water (2×5 ml) and evaporated to give (+,−)-1-benzyl-3-hydroxymethyl-4-(4-fluorophenyl)-1,2,3,6-tetrahydropyridine (ee 5.48%).

What is claimed is:

1. A process for the racemisation of a compound of formula I comprising the steps of a) reacting an enantiomerically enriched compound of formula I

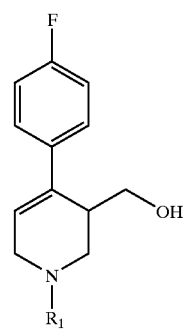

I in which $R_1$ represents an amine protecting group, with a compound of formula II $R_2X$  II in which $R_2$ represents a group of formula $R_3SO_2$—in which $R_3$ represents optionally substituted phenyl, a $C_{1-6}$alkyl group or a trifluoromethyl group and X represents halo to give a compound of formula III

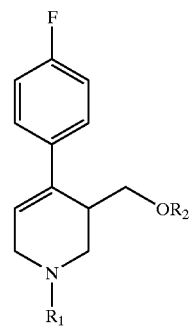

III in which i) $R_2$ represents a group of formula $R_3SO_2$—
in which $R_3$ represents optionally substituted phenyl, a $C_{1-6}$alkyl group or a trifluoromethyl group, b) reacting the compound of formula III with a compound of formula IV

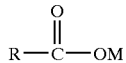

IV in which M represents an alkali metal and R represents H, a $C_{1-6}$alkyl group, optionally substituted phenyl or an (optionally substituted phenyl)hydroxy$C_{1-6}$alkyl group to give a substantially racemic compound of formula V

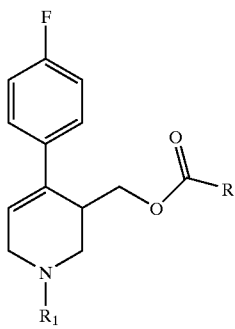

V in which $R_1$ and R are as previously defined; and c) reacting the compound of formula V with a hydrolysing agent to give a substantially racemic compound of formula I.

2. A process for the racemisation of a compound of formula I comprising the steps of a) reacting an enantiomerically enriched compound of formula I

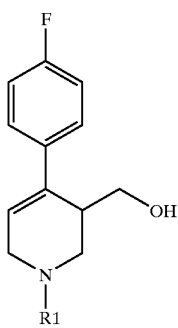

I in which $R_1$ represents an amine protecting group, with a compound of formula II

II in which $R_2$ represents a group of formula $R_3SO_3$—in which $R_3$ represents optionally substituted phenyl, a $C_{1-6}$alkyl group or a trifluoromethyl group and X represents halo to give a compound of formula III

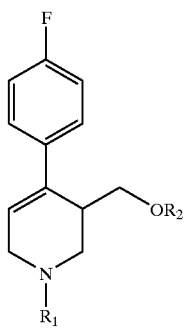

III in which i) $R_2$ represents a group of formula $R_3SO_2$—in which $R_3$ represents optionally substituted phenyl, a $C_{1-8}$alkyl group or a trifluoromethyl group, wherein the compound of formula III is in equilibrium with a compound of formula IIIa

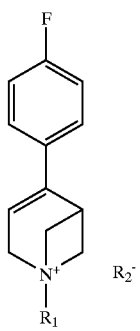

IIIa in which $R_1$ represents an amine protecting group and $R_2^-$ is an anion of $R_2$ b) reacting the compound of formula IIIa with a compound of formula IV

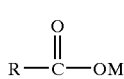

IV in which M represents an alkali metal and R represents H, a $C_{1-6}$alkyl group, optionally substituted phenyl or an (optionally substituted phenyl)hydroxy$C_{1-6}$alkyl group to give a substantially racemic compound of formula V

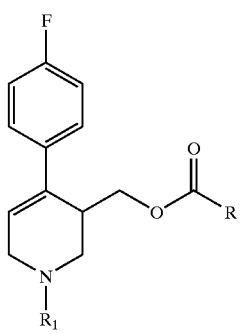

V in which $R_1$ and R are as previously defined; and c) reacting the compound of formula V with a hydrolysing agent to give a substantially racemic compound of formula I.

3. A process according to claim 1 in which the amine protecting group is selected from a) allyl, b) benzhydryl, c) methoxymethyl, d) benzyloxymethyl, e) tetrahydropyranyl, f) an optionally substituted benzyl group, g) di(p-methoxyphenyl)methyl, h) triphenylmethyl, i) (p-methoxyphenyl)diphenylmethyl, j) diphenyl-4-pyridylmethyl, k) a $C_{1-6}$alkyl group, for example methyl or ethyl, l) a trifluoro $C_{1-4}$alkyl group, m) an alkynyl group or n) p-methoxybenzyl.

4. A process according to claim 1 in which $R_3$ represents methyl or phenyl optionally substituted by a methyl, group, a nitro group or halo.

5. A process according to claim 1 in which the hydrolysing agent is selected from one or more of the following: aqueous sodium hydroxide, aqueous ammonia, aqueous potassium carbonate, aqueous potassium bicarbonate, aqueous sodium bicarbonate, aqueous sodium carbonate, potassium hydroxide, aqueous potassium hydroxide and aqueous lithium hydroxide.

6. A compound of formula IIIa

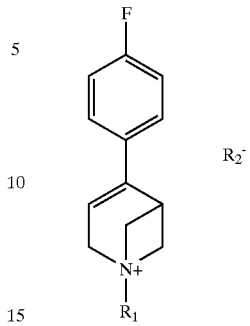

in which $R_1$ represents an amine protecting group and $R_2$ represents a group of formula $R_3SO_2$— in which $R_3$ represents optionally substituted phenyl, a $C_{1-6}$alkyl group or a trifluoromethyl group.

7. A compound according to claim 6 in which $R_1$ represents benzyl or a $C_{1-6}$ alkyl group.

* * * * *